United States Patent [19]
Cipolletti

[11] Patent Number: 5,489,311
[45] Date of Patent: Feb. 6, 1996

[54] PROSTHESIS WITH ORIENTABLE BEARING SURFACE

[75] Inventor: George B. Cipolletti, Wilton, Conn.

[73] Assignee: Joint Medical Prducts Corporation, Stamford, Conn.

[21] Appl. No.: 184,274

[22] Filed: Jan. 21, 1994

[51] Int. Cl.⁶ ..................................................... A61F 2/38
[52] U.S. Cl. ............................................. 623/20; 623/18
[58] Field of Search ................................ 623/16, 18, 20; 606/86, 87, 88, 99

[56] References Cited

U.S. PATENT DOCUMENTS

| | | |
|---|---|---|
| 4,219,893 | 9/1980 | Noiles . |
| 4,678,472 | 7/1987 | Noiles . |
| 5,002,578 | 3/1991 | Luman . |
| 5,152,796 | 10/1992 | Slamin ..................................... 623/20 |
| 5,194,066 | 3/1993 | Van Zile ................................... 623/20 |
| 5,282,864 | 2/1994 | Noiles et al. . |

FOREIGN PATENT DOCUMENTS 2154338  5/1973  Germany .

OTHER PUBLICATIONS

Translation of Patent No. 2,154,338 (Germany, May 17, 1973), Item No. 5 above.

*Primary Examiner*—David Isabella
*Attorney, Agent, or Firm*—Maurice M. Klee

[57] ABSTRACT

A prosthesis (13) for implantation in a patient's bone (2) is provided which has a metal fixation member (10), a metal orienting member (20) secured to the fixation member (10) by a self-locking taper (15,24), and a plastic bearing (30) which is secured to the orienting member (20) in a predetermined orientation. By means of this structure, the plastic bearing (30) can be given a desired orientation with regard to the metal fixation member (10) independent of the orientation of the fixation member (10) with respect to the patient's bone (2). Also, replacement and/or reorientation of the bearing (30) are facility. The prosthesis (13) can be used to form the tibial component of an artificial knee joint.

8 Claims, 3 Drawing Sheets

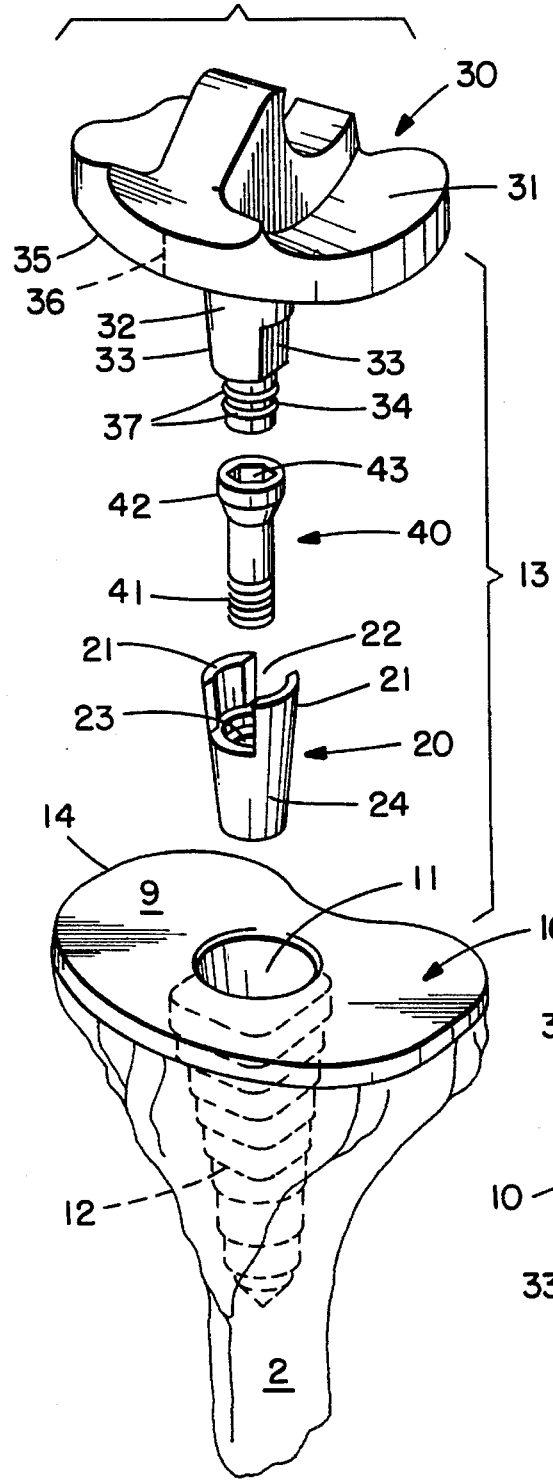
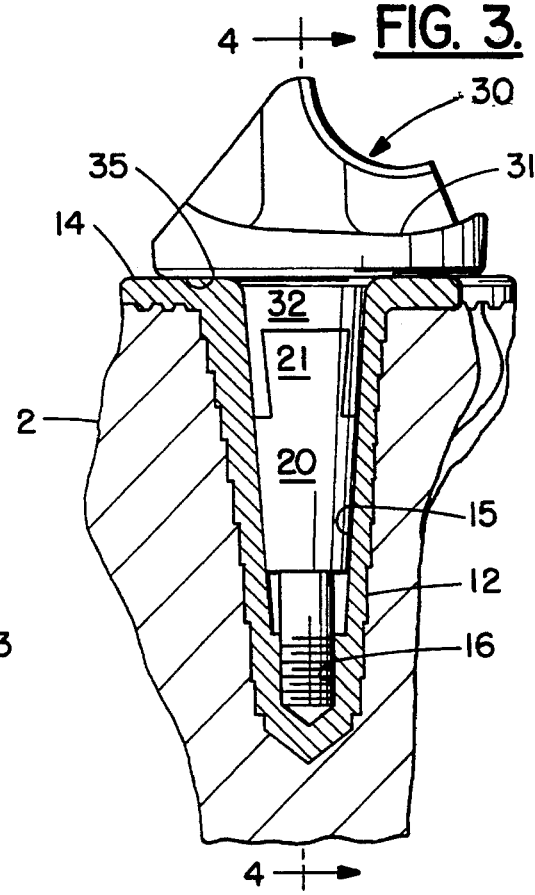
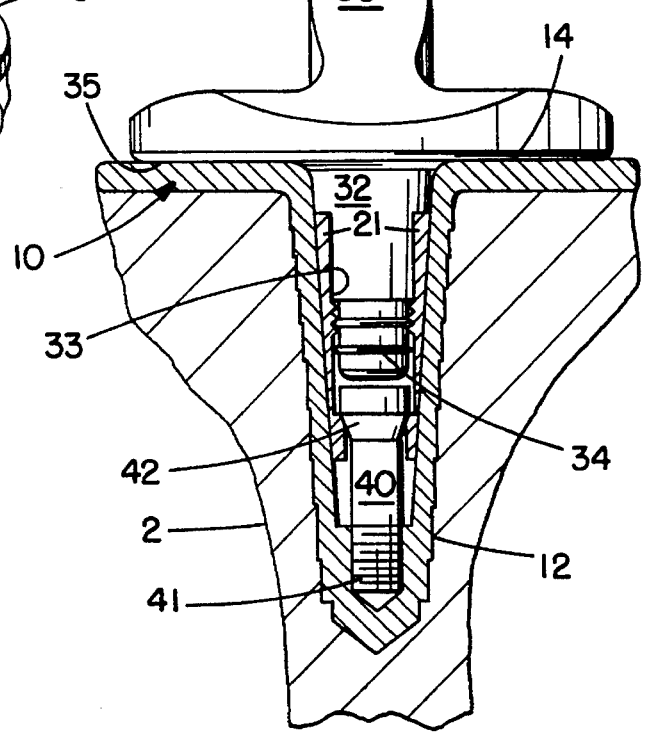

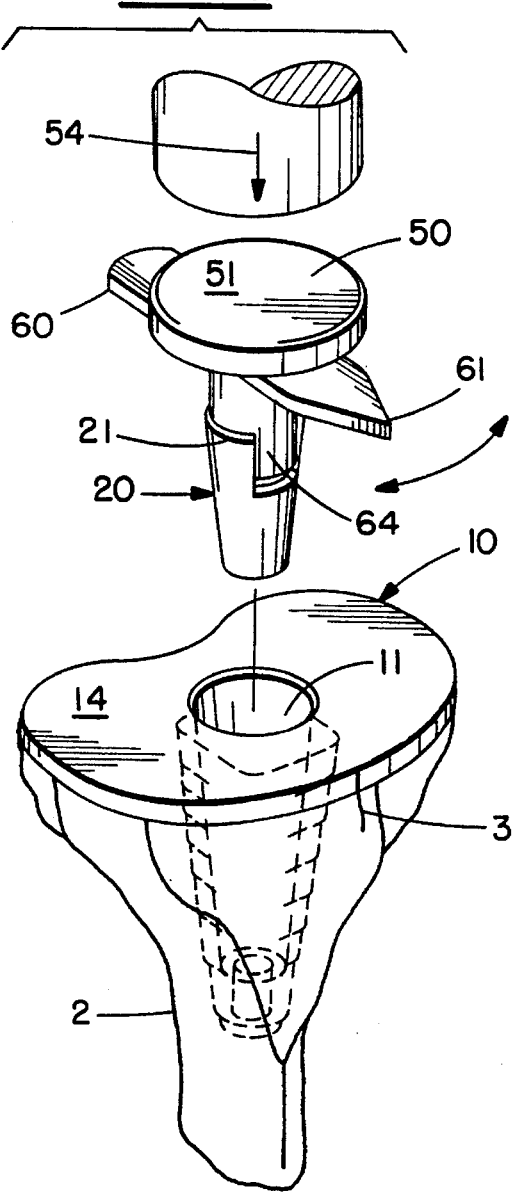
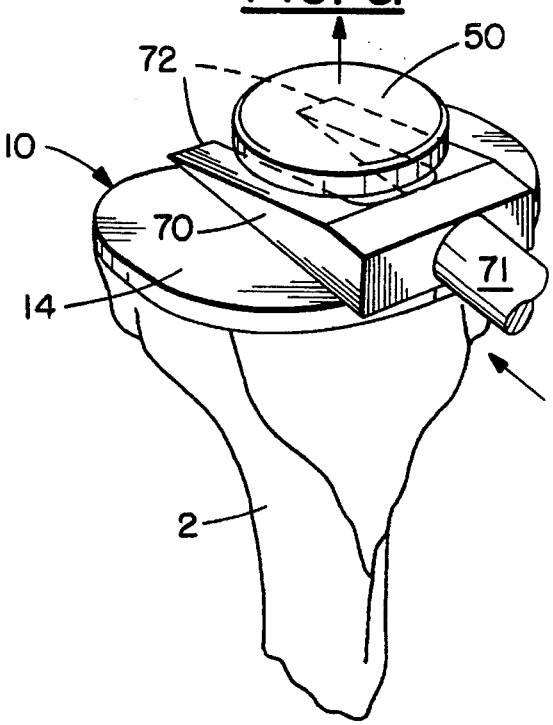
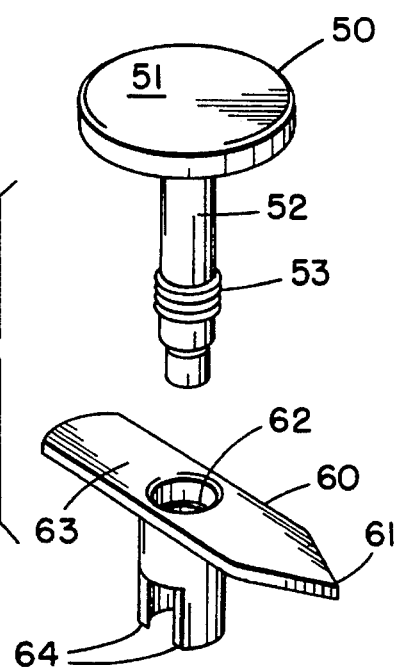

5,489,311

PROSTHESIS WITH ORIENTABLE BEARING SURFACE

BACKGROUND OF THE INVENTION

1. Field of the Invention

This invention relates to implantable joint replacement prostheses and, in particular, to a prosthesis having a bearing surface which is orientable. In its preferred embodiments, the prosthesis serves as the tibial component of an artificial knee joint.

2. Description of the Prior Art

Hartmann, German Patent Publication No. 2,154,338, discloses a hinged artificial knee joint having a tibial shaft 2' which includes a tapered bore 3' which receives conical pin 3 of hinge support 1. By means of the tapered bore and the conical pin, the hinge support can be rotated at the time of implantation for "correction" of the alignment of the tibial and femoral components of the joint. A screw 4 which engages a threaded borehole 11' in tibial shaft 2 is used to fix the hinge support within the tibial shaft.

Contemporary artificial knee joints commonly include a bearing element composed of a deformable material, e.g., a plastic such as ultra high molecular weight polyethylene. Such elements provide bearing function generally accepted in the art.

The construction shown in the Hartmann reference contains no provision for the use of such a bearing element composed of a deformable material. In particular, Hartmann's joint requires that hinge support 1 and tibial shaft 2 be composed of non-deformable materials, such as metals, so that these components can be held together in a fixed relation by screw 4. Prostheses having all metal constructions currently have little use in the art.

A tibial prosthesis for a knee joint which has been sold by Joint Medical Products Corporation, the assignee of this application, is shown in FIG. 7. As shown therein, this prosthesis includes: 1) tibial fixation member 100 composed of metal and having an internal conical bore 102; 2) tibial bearing member 104 composed of metal and having projecting conical shaft 106 for locking engagement with bore 102; 3) cap 110 for sealing the distal end of fixation member 100; 4) screw 108 for holding cap 110 and members 100 and 104 together; and 5) tibial plateau bearing member 112 composed of ultra high molecular weight polyethylene and having shaft 114 which is received in internal bore 116 of tibial bearing member 104. Conical bore 102 and conical shaft 106 form a self-locking taper. Because of the clearance between them, conical bore 116 and conical shaft 114 do not form a locking taper so that tibial plateau bearing member 112 is free to rotate on tibial bearing member 104.

Although this commercial construction has worked well in practice, it does not provide a fixed relationship between tibial plateau bearing member 112 and fixation member 100 which is desired for some patients.

SUMMARY OF THE INVENTION

In view of the foregoing state of the art, it is an object of the present invention to provide a system for orienting a prosthetic component having a bearing surface relative to a fixation means where the component is composed of a deformable material. In particular, it is an object of the invention to provide such a system for use in forming the tibial component of an artificial knee joint.

To achieve the foregoing and other objects, the invention in accordance with certain of its aspects provides a prosthesis for implantation in a bone (e.g., the tibia), said prosthesis having a bearing surface and comprising a first member (a "fixation means") for implantation in the bone, a second member (an "orienting means") which mates with the first member through a self-locking taper, and a third member (a "bearing member") which carries the bearing surface, wherein:

(a) the first member has a conical bore, a portion of which forms the female part of the self-locking taper;

(b) the second member has an outer surface a portion of which has a conical surface and forms the male part of the self-locking taper, said second member:
   (i) being receivable in the bore of the first member; and
   (ii) including means for rotating the second member within the bore of the first member prior to locking engagement of the self-locking taper; and (c) the third member has means for engaging the second member in a predetermined angular orientation.

In the preferred embodiments of the invention, the third member's means for engaging engages the second member's means for rotating.

Prosthetic joints constructed in accordance with the invention provide the important advantage that the fixation means can be implanted in the patient's bone based on the anatomy of that bone to provide the best possible interface with and coverage of the bone without regard to the alignment/orientation of the prosthesis' bearing surface, and then, after the fixation means has been implanted, the orientation of the bearing surface can be optimized by selecting the orientation of the orienting means (second member) relative to the fixation means.

In accordance with certain of its preferred embodiments, the prosthesis includes a screw for providing additional securement of the second member to the first member in addition to that provided by the self-locking taper. In accordance with other preferred embodiments, the second member includes a bore having a female thread formed therein for inserting and removing the second member from the first member.

In accordance with others of its aspects, the invention provides apparatus for use in orienting the second member of the prosthesis relative to the first member after the first member has been implanted in the patient's bone. This apparatus comprises:

means for indicating the angular orientation of the second member relative to the first member; and means for releasably engaging the means for rotating the second member.

In certain preferred embodiments of these aspects of the invention, the apparatus includes a drive member for locking the first and second members together by means of the locking engagement of the self-locking taper.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

FIG. 1 is an exploded, perspective view of a tibial prosthesis constructed in accordance with the invention.

FIG. 2 is an exploded view illustrating the assembly and alignment of second member 20 with first member 10.

FIG. 3 is a cross-sectional, sagittal view of the assembled prosthesis of FIG. 1.

FIG. 4 is a cross-sectional, coronal view of the assembled prosthesis of FIG. 1 along lines 4—4 in FIG. 3.

FIG. 5 illustrates a procedure for extracting second member 20 from first member 10.

FIG. 6 is an exploded, perspective view of apparatus for aligning the second member relative to the first member and for engaging the self-locking tapers carried by those members.

DESCRIPTION OF THE PREFERRED EMBODIMENTS

Figure 7:
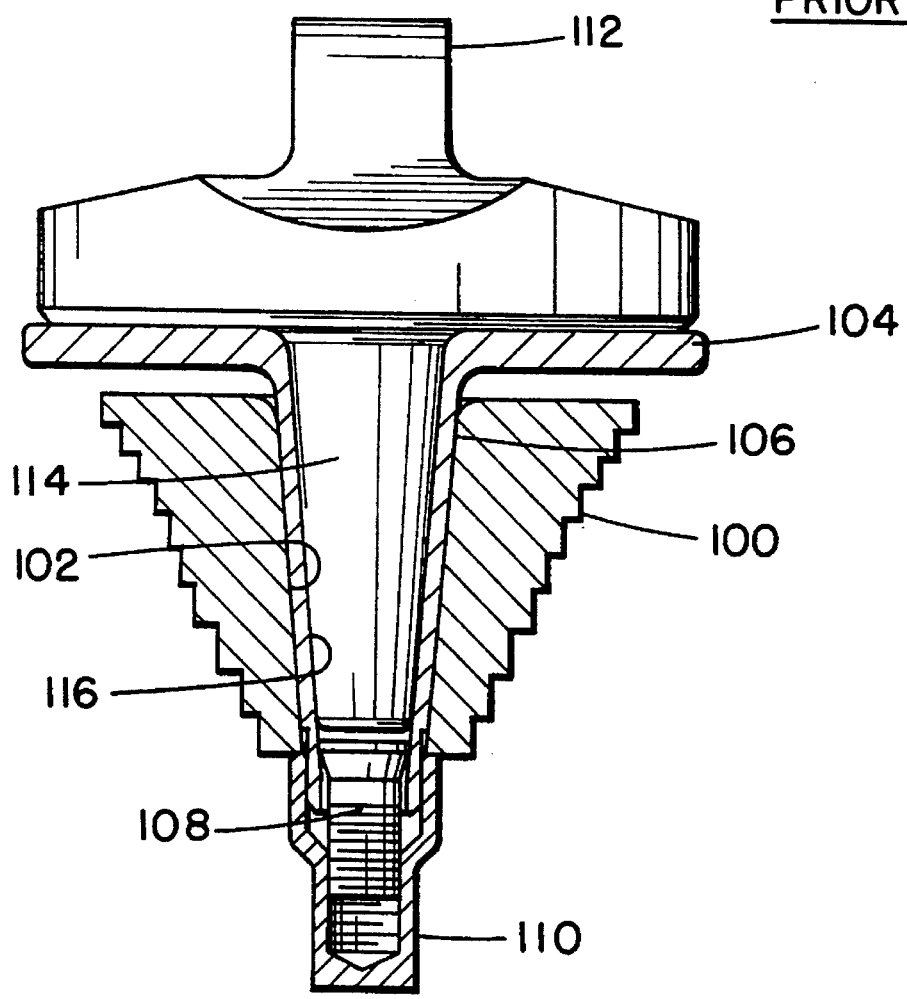
FIG. 7 is a cross-sectional, coronal view of a prior art tibial prosthesis.

With reference now to the drawings, wherein like reference characters designate like or corresponding parts throughout the several views, there is shown in FIG. 1 an exploded view of a tibial prosthesis 13 constructed in accordance with the invention. The prosthesis includes first member 10 having an outer surface 12 for engagement with and fixation to the bone of the patient's tibia 2.

First member 10 includes bore 11 having a female self-locking conical taper 15 formed therein. The first member also includes flange 9 which engages and covers the resected proximal end of tibia bone 2.

Second member 20 is received in bore 11 of first member 10. This member has a male self-locking conical taper 24 for engagement with the female self-locking conical taper 15 of bore 11. To ensure a secure fit between these components, the taper angle of these conical surfaces is chosen to be within the range of self-locking tapers. For example, a total included taper angle (both sides of the taper) in the range of from about 3° to about 17° will achieve this result. More generally, the total included taper angle $\alpha$ must satisfy the following relationship where $\mu$ is the coefficient of friction between the materials making up the male and female surfaces of the taper:

$$\tan \alpha/2 < \mu.$$

In practice, a total included taper angle of about 8° has been found to work successfully.

Second member 20 also includes female thread 23 and through slot 22 bounded by tabs 21. Thread 23 is used in removing second member 20 from first member 10 using drive member 50 (see discussion below). Through slot 22 and tabs 21 are used in orienting second member 20 relative to first member 10 by means of alignment apparatus 60 as discussed below. Thread 23, slot 22, and tabs 21 also receive and engage protrusion 34 and flats 33 formed in projection 32 of third member 30.

Screw 40 serves to provide additional securement of second member 20 to first member 10 in addition to that provided by self-locking tapers 15 and 24. The screw includes a head 42 having a hexagonal driving socket 43. It also includes male thread 41 which passes freely through thread 23 of second member 20 to engage female thread 16 formed in the distal end of bore 11 of first member 10.

Third member 30 includes bearing surface 31 for mating with a complementary bearing surface of the femoral component of the artificial joint (not shown). This member is composed of a deformable material such as ultra high molecular weight polyethylene. The member includes distal surface 35 which rests on surface 14 of first member 10 in the assembled joint.

The apparatus of the invention is used as follows. First, the patient's bone is prepared to receive first member 10 and that member is implanted with or without bone cement using conventional surgical techniques known in the art. In performing this implantation, aside from the requisite axial alignment with the tibia, the surgeon need only be concerned with achieving the optimum coverage and interface between member 10 and bone 2. In particular, the surgeon is free to rotate flange 9 to obtain maximum coverage of the distal end of tibia bone 2 without concern for the orientation of bearing surface 31 since by means of the invention, the orientation of that surface is achieved separately from the orientation of member 10 including its flange 9.

Once member 10 is implanted, the surgeon uses a "trial" member 30 (not shown) to determine the desired orientation of bearing surface 31 for the particular needs of the patient. This trial member generally has a simplified shaft 32 without protrusion 34 or flats 33. It also includes an index mark 36 along its centerline for use by the surgeon in marking the patient's bone and/or first member 10 to indicate the desired orientation of member 30 (see dotted line 36 in FIG. 1 with regard to the index mark on the trial member and line 3 in FIG. 2 with regard to the mark on the bone and/or first member 10).

Once the desired orientation has been established and the bone marked, the trial member 30 is removed and second member 20 is inserted into bore 11 using alignment instrument 60 and driving member 50 (see FIGS. 2 and 6). Driving member 50 includes male thread 53 which is screwed totally through female thread 62 in alignment instrument 60 and then is screwed into female thread 23 in second member 20 so that tangs 64 of the alignment instrument 60 engage with slot 22 of second member 20. In this way, the orientation of second member 20 with respect to alignment instrument 60 is fixed.

The surgeon then aligns pointer 61 of alignment instrument 60 with alignment mark 3 previously made on the patient's bone and/or first member 10. Driving member 50 is designed so that head 51 stands proud of indicating blade 63 when the driving member, alignment instrument 60, and second member 20 are assembled. In this way, after second member 20 has been aligned to the desired orientation using pointer 61, the locking tapers on the first and second member can be placed into locking engagement by a hammer blow to head 51 (see arrow 54 in FIG. 2).

Once the locking tapers have been lockingly engaged, drive member 50 is unscrewed from second member 20 and the drive member and attached alignment instrument 60 are removed. Screw 40 is then passed through second member 20 and tightened into thread 16 of first member 10. Finally, third member 30 is engaged with second member 20 by 1) the alignment of flats 33 with tabs 21, and 2) the driving of deformable ribs 37 on protrusion 34 into female thread 23 of second member 20.

Prosthesis 13 can be readily disassembled if necessary to, for example, reorient or replace third member 30. Disassembly is performed as follows. First, tapered wedge 70 is used to break the bond between deformable ribs 37 and female thread 23. In this disassembly, forks 72 are driven between mating surface 35 of third member 30 and surface 14 of first member 10. Once this bond has been broken, the third member is removed. If only replacement is to be done, without reorientation, a new third member is assembled into the joint as described above.

If reorientation is required, screw 40 is removed and thread 53 of drive member 50 is threaded into female thread 23 of second member 20. Forks 72 are then driven between head 51 and surface 14 of first member 10 by means of drive shaft 71. This causes the self-locking taper between surfaces 24 and 15 to release, thus allowing reorientation (or removal and replacement) of second member 20. Reassembly of the joint then follows the procedures described above.

The components of the prosthesis can be constructed of various biocompatible materials suitable for implantation now known or subsequently developed. For example, first member 10, second member 20, and screw 40 can be made of a cobalt-chromium-molybdenum alloy (see ASTM-F75 and ASTM-F799) or a titanium alloy such as Ti 6Al 4 V (ASTM-F136). As discussed above, third member 30 is composed of a deformable material such as ultra high molecular weight polyethylene.

Although specific embodiments of the invention have been described and illustrated, it is to be understood that modifications can be made without departing from the invention's spirit and scope. For example, the invention has been described in the context of an artificial knee joint, but can also be used for other artificial joints such as an elbow joint. A variety of modifications may be perceived by those skilled in the art without departing from the scope of the invention as defined by the following claims.

What is claimed is:

1. A prosthesis for implantation in a bone, said prosthesis having a bearing surface and comprising a first member for implantation in the bone, a second member which mates with the first member through a self-locking taper, and a third member which carries the bearing surface, wherein:

(a) the first member has a bore, a portion of which forms a female part of the self-locking taper;

(b) the second member has an outer surface a portion of which forms a male part of the self-locking taper, said second member:

(i) being receivable in the bore of the first member; and (ii) including means for rotating the second member within the bore of the first member prior to locking engagement of the self locking taper; and (c) the third member has means for engaging the second member in a predetermined angular orientation relative to the second member and for preventing the third member from rotating relative to the second member.

2. The prosthesis of claim 1 wherein the second member includes a bore having a female thread formed therein for removing the second member from the first member.

3. The prosthesis of claim 1 further comprising a screw for securing the second member to the first member.

4. The prosthesis of claim 3 wherein the second member includes a bore and the screw is received within the bore.

5. The prosthesis of claim 1 wherein the third member's means for engaging and preventing rotation engages the second member's means for rotating.

6. A system comprising the prosthesis of claim 1 and an apparatus for implanting the prosthesis, said apparatus comprising:

means for indicating the angular orientation of the second member relative to the first member; and means for releasably engaging the means for rotating the second member.

7. The system of claim 6 wherein the means for indicating and the means for releasably engaging are rotatably mounted on a drive member for locking the engagement of the self-locking taper.

8. The system of claim 6 wherein the means for indicating and the means for releasably engaging comprise a unitary element which is rotatably mounted on a drive means for locking the self-locking taper.

* * * * *